United States Patent [19]

Mattes et al.

[11] Patent Number: 4,963,469
[45] Date of Patent: Oct. 16, 1990

[54] ENZYMATICALLY INACTIVE, IMMUNOLOGICALLY-ACTIVE β-GALACTOSIDASE MUETIN, PROCESS FOR MAKING AND USES THEREOF

[75] Inventors: Ralf Mattes, Stuttgart; Helmut Lenz, Tutzing; Werner Stock, Gräfelfing, all of Fed. Rep. of Germany

[73] Assignee: Boehringer Mannheim GmbH, Mannheim, Fed. Rep. of Germany

[21] Appl. No.: 218,816

[22] Filed: Jul. 12, 1988

[30] Foreign Application Priority Data

Jul. 24, 1987 [DE] Fed. Rep. of Germany ....... 3724625

[51] Int. Cl.$^5$ ................... G01N 33/53; G01N 33/563; C07K 3/00
[52] U.S. Cl. .......................................... 435/7; 435/14; 435/18; 435/172.1; 435/181; 435/188; 435/207; 436/512; 436/532; 436/537; 530/388; 530/402
[58] Field of Search .................... 435/7, 14, 18, 172.1, 435/181, 188, 207; 436/512, 532, 537; 530/388, 402

[56] References Cited

U.S. PATENT DOCUMENTS 4,446,233  5/1984  Auditore-Hargreaves et al. ..................................... 436/547 X
4,668,620  5/1987  Armenta et al. .................. 435/14 X
4,810,635  3/1989  Ledden et al. .................. 436/825 X

OTHER PUBLICATIONS

Ring et al. "Site–Directed Matagenesis of β–Galactosidase . . . ", Biochem. Biophys. Res. Comm. 152(3), 1050–5(5/1988).
Fowler et al., "Methionine 500, the Site of Covalent Attachment . . . β–Galactosidase", J. Biol. Chem. 253(190), 5283–5285(8/10/78).

Primary Examiner—Elizabeth C. Weimer
Assistant Examiner—Carol A. Spiegel
Attorney, Agent, or Firm—Felfe and Lynch

[57] ABSTRACT

The present invention provides an enzymatically-inactive, immunologically-active β-galactosidase mutein, wherein, in the region between the amino acids 430 and 550, at least one amino acid of the natural sequence is changed to another amino acid and the enzymatic activity does not amount to more than 1%, referred to the native enzyme. The present invention also provides a process for the production of this mutein. Furthermore, the present invention is concerned with the use of this mutein in the immunological determination of serum proteins by the enzyme immunoassay principle.

22 Claims, 6 Drawing Sheets

1. Gal mutein (Ala 461)
2. Gal mutein (Asp 461)
3. Gal mutein (Glu 503)
4. native β-Galactosidase
5. Gal mutein (Ala 503 / Phe 461)

Gal mutein ( Glu 503 )

native β-Galactosidase

ENZYMATICALLY INACTIVE, IMMUNOLOGICALLY-ACTIVE β-GALACTOSIDASE MUETIN, PROCESS FOR MAKING AND USES THEREOF

The present invention is concerned with enzymatically-inactive, immunologically-active β-galactosidase muteins, with processes for the preparation thereof and with the use thereof for enzyme immuno-assays (EIA) with β-galactosidase as labelling enzyme for the removal of serum interference and for lowering non-specific blank values.

It has been observed that, in the case of enzyme immuno-assays, human sera with a low content of the actual analyte sometimes give high signals. This interference can be traced back to serum factors which enter into bonding with a conjugate of anti-analyte-antibodies and β-galactosidase which do not correspond to the actual, intended anti-analyte binding function of the conjugate. Consequently, false analyte values are attributed to such sera.

Enzyme immuno-assays can be carried out in various ways. They are possible not only as heterogeneous sandwich processes but also in homogeneous soluble phase.

In the case of the use of the sandwich process, the determination of the amount of desired serum protein is simple: the antigen-antibody-enzyme complex present in solid phase is separated off from supernatant liquid and the enzyme activity subsequently measured.

However, the measurement of the amount of the serum protein in question is more difficult in the case of homogeneous enzyme immuno-assays with the use of β-galactosidase. Other possibilities can be chosen: for example a colorimetric enzyme inhibition immunoassay (Gibbons et al., in Immobilized Enzymes and Cells, Methods in Enzymology, K. Moosbach ed., pub. Academic Press, New York), a turbidometric enzyme activation immunoassay (Gibbons et al., Clin. Chem., 27, 16002/1981) and the more sensitive fluorimetric enzyme inhibition immunoassay (Armenta et al., Anal. Biochem., 1985).

However, in the case of all methods, interference factors in the serum, i.e. proteins which bind to the β-galactosidase molecule itself or to the anti-analyte-antibody bound therewith or also to the binding sites thereof, as well as inhibitors of the β-galactosidase activity present therein, considerably impair the quantitative determination. Such inhibitors can be anti-β-galactosidase antibodies, which inhibit the enzyme activity by blocking the active center for the macromolecular substrate of the enzyme.

In order to prevent impairment of the precision of the enzyme immunoassay, several methods have been developed. Thus, the antibody-enzyme complex has been "protected" against anti-enzyme antibodies by the coupling of several albumin molecules to the enzyme. Interestingly, this can be carried out without impairment of the enzyme activity. However, this possibly causes steric inhibition of the binding of an anti-enzyme-antibody and the desired binding of the protein to be determined. Furthermore, it is known to use in excess unconjugated, inactive β-galactosidase derivatives which display the native antigenic character of the enzyme in order to prevent the binding of the antienzyme antibody to the active β-galactosidase. However, with this method, too, the test cannot be carried out with the desired accuracy.

Therefore, it is an object of the present invention to overcome the above-described difficulties and to provide a method for the elimination of the interference factors from sample serum.

Thus, according to the present invention, there is provided an enzymatically-inactive, immunologically-active β-galactosidase mutein protein, wherein, in the region between the amino acids 430 and 550, at least one amino acid of the natural sequence is exchanged for another amino acid and the enzymatic activity does not amount to more than 1%, referred to the native enzyme.

In a preferred embodiment, this amino acid exchange takes place on the amino acids Glu 461 and/or on the amino acid Tyr 503. Thus, for example, the amino acid Glu 461 can be substituted by one of the amino acids Ser, Ala, Asp or Tyr and/or the amino acid Tyr 503 by one of the amino acids Phe, Glu or Ser. However, substitution of other amino acids is also possible. Due to this amino acid exchange in the given region, the enzyme activity is reduced to 1% and preferably to 0.1% of the enzyme activity of the native β-galactosidase but the immunological activity of the β-galactosidase is not impaired.

The preparation of these β-galactosidase muteins can be carried out in various ways. According to the present invention, the preparation is carried out via site-directed mutagenesis of a plasmid coding for β-galactosidase on the DNA plane at the appropriate places and subsequent expression in appropriate hosts. The site-directed mutagenesis can favorably be brought about according to the heteroduplex technique of Morinega et al., Biotechnology, Jul., 1984, 636/1984. For this purpose, a plasmid coding for β-galactosidase is cleaved with restriction endonucleases in two different ways: on the one hand, by cleavage with the enzymes A and B, the region coding for β-galactosidase is cut out from the plasmid, producing a linear plasmid remaining which does not contain the β-galactosidase coding sequence; on the other hand, the same plasmid is cleaved with a restriction enzyme C which cleaves outside of the region coding for β-galactosidase, the plasmid thereby being linearized. Then, by denaturing by heating, melting of the double-stranded DNA structure is brought about which results in the formation of single-stranded DNA chains. The solution of the single-stranded DNA fragments is added to a phosphorylated oligonucleotide which represents a small part of the β-galactosidase sequence but, at the position of the desired amino acid exchange, contains a mutation of a base of the triplet coding for the amino acid. After renaturing the single-strand DNA mixture containing the oligonucleotide by stepwise cooling, four different double-stranded DNA molecules I, a, b and II can be formed. The double-stranded DNA molecules I and II only represent the reformation of the starting molecules by hybridization. In the case of the molecules a and b, the two part strands of the starting molecules are not again combined with one another but rather, in each case, a single strand of the starting molecules I and II. Therefore, double-stranded DNA molecules result which are single-stranded in the region coding for β-galactosidase. Therefore, on the molecule a, which contains the complementary strand for the DNA sequence of the oligonucleotide, the oligonucleotide can adhere by hybridization but in the region of the base exchange a so-called "mismatch" thereby results. By means of the addition of DNA polymerase I and 4 desoxynucleotides, as well as of T$_4$-DNA ligase, the remaining single-stranded regions are filled and the double-stranded DNA closed.

It is especially favorable to carry out the base exchange in such a manner that, in the corresponding plasmid, the cleavage pattern in the case of digestion with a restriction enzyme is changed, so that after transformation, selection of the colonies containing the mutated plasmid is simplified. This can take place either by destruction or introduction of a restriction cleavage point for a restriction enzyme by choice of an appropriate base. However, the evaluation of the colonies can also be carried out via other known techniques, such as hybridization analysis (colonies/plasmids), coloration of the colonies with X-Gal, SDS gel electrophoresis of whole cell extracts, immunoassays with sheep anti-β-Gal-IgG-POD (peroxidase) conjugate, native gel electrophoresis or enzyme activity tests with various other colored substrates. The colonies containing the mutated plasmid (positive) are further multiplied, in which case the cell-inherent repair mechanism can repair the "mismatch" in two ways, so that, on the one hand the mutant plasmid results or, on the other hand, wild type plasmid again results. The newly obtained colonies are assessed according to the above-mentioned techniques and the mutant plasmid is used for expression of the β-galactosidase muteins in appropriate host cells. It has been ascertained that, in the case of all of the amino acid exchanges carried out in the following examples, the aggregation of the β-galactosidase mutein monomers to tetramers is not impaired.

The β-galactosidase muteins are used together with the Fab part of an immunoglobulin which, however, is not binding-active for the analyte. In this way, disturbing factors possibly present in the serum directed against binding-active Fab parts of the anti-analyte immunoglobulin, as well as disturbing factors which are directed against the β-galactosidase protein, can be intercepted. It is possible to use a conjugate of components enzymatically inactive β-galactosidase mutein and non-analyte binding immunoglobulin Fab, where the components have been bound in the same way the "active" conjugate has been bound (e.g., via N-maleinimidohexanoyl-O-succinimide). When this bound, "inactive" conjugate is used rather than non-chemically bound mutein and Fab, the precision of the assay is improved. This is because interference factors which are directed against the bridge builder itself or the connecting points of the bridge and the two bridged components, or the Fab portion of the enzymatically active conjugate, are inhibited. Expressed another way, the reaction of these interference factors with the "inactive" conjugate removed interference with the active conjugate.

The present invention also provides a reagent for enzyme immunoassays (EIA) with β-galactosidase as labelling enzyme for the removal of serum interference factors and for lowering non-specific blank values, wherein it contains an enzymatically-inactive, immunologically active β-galactosidase mutein and, when it is used together with the Fab part of an analyte non-binding immunoglobulin, possibly in chemically bound form, the conjugate of mutein-non-analyte binding Fab possesses properties which enable it to bind to serum interference factors. As it is not enzymatically or anti-analyte active, however, this conjugate intercepts the interference factors without impairing either enzymatically active β-galactosidase or the anti-analyte immunoglobulin. In this way, serum interference factors are intercepted and can no longer impair the subsequent determination with enzymatically-active β-galactosidase.

DETAILED DESCRIPTION OF PREFERRED EMBODIMENTS

EXAMPLE 1

Figure 1:
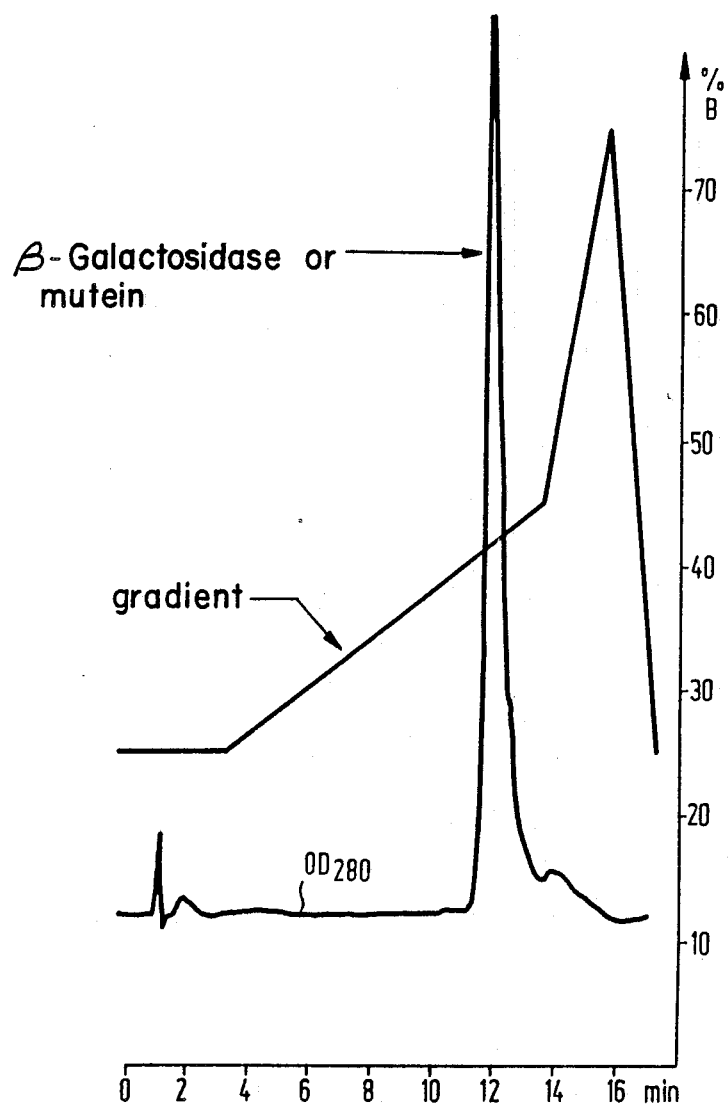
FIG. 1 is an anion exchange chromatogram according to Example 2.3.1.

The molecular-biological standard methods, for example transformation, restriction and plasmid isolation, are carried out according to T. Maniatis, E. F. Fritsch and J. Sambrook, *Molecular Cloning*, Cold Spring Harbor Laboratory, New York 11724, 1982.

Construction of β-Gal mutein genes (1a) Preparation of the starting plasmid

From the genes of the Escherichia coli phage λplac 5-1 (DSM 4176)), described by C. Pourcel et al. in Molec. gen. Genet., 170, 161–169/1979, there is obtained, by cleavage with the restriction enzyme Bst EII, an approximately 5.2 kb fragment which is recovered preparatively by gel electrophoresis. The plasmid pACYC 177 (DSM 369P) is linearized by cleavage with the enzyme Pst I. The ends of the lacZ-carrying, approximately 5.2 kb sized Bst EII fragment from λplac 5-1 are blunt end digested with the use of the enzyme nuclease S1 and, with the help of the enzyme terminal transferase and dCTP, lengthened by any desired number of d-cytidine residues (for a description of the process, see Maniatis et al., pages 217–246). The pACYC 177 molecule linearized with Pst I is, with the use of the enzyme terminal transferase and GTP, lengthened on the 3' end by any desired number of d-guanidine residues. The mixture of both thus lengthened fragments is combined and so introduced by transformation into *Escherichia coli* cells of the strain BMTU 2489 (DSM 4178). The *Escherichia coli* cells are selected on nutrient medium which contains 25 μg/ml of kanamycin and 40 μg/ml of 5-bromo-4-chloro-3-indolyl-β-D-galactosidase (X-Gal). From the cells which are blue and sensitive towards 50 μg/ml ampicillin, the plasmid is isolated in which both ends of the original Bst EII fragment are lengthened by 15 G/C pairs. This plasmid is used as starting plasmid. This differs from λplac 5-1 and pACYC 177 in that, by cleavage with Pst I, it allows one to obtain fragments, the larger of which contains the lacZ gene fragment from λplac 5-1.

Cells of Escherichia coli which contain the starting plasmid produced β-Gal constitutively.

Plasmids in which both ends of the Bst EII fragment are lengthened by 5 to 30 G/C pairs can also be used as starting plasmids.

(1a') Preparation of an alternative starting plasmid

From the genes of the Escherichia coli phages λplac 5-1 (DSM 4176P), by cleavage with the restriction enzyme Bst EII, there is obtained an approximately 5 kb fragment which is recovered preparatively by gel electrophoresis. The plasmid pACYC 177 (DSM 3993P) is linearized by cleavage with the enzyme Pst I. The ends of the lacZ-carrying, approximately 5 kb sized Bst EII fragment from λplac 5-1 are blunt end digested with the use of the enzyme nuclease S1. The two fragments are ligated and transformed into Escherichia coli.

The Escherichia coli cells are selected on nutrient medium which contains 25 μg/ml of kanamycin and 40 μg/ml 5-bromo-4-chloro-3-indolyl-β-D-galactosidase (X-Gal). Cells which are blue and sensitive towards 50 μg/ml ampicillin are selected. These cells each contain one of two different plasmids. These plasmids differ by the orientation of the Bst EII fragment and consequently give different cleavage patterns with Bam HI and Eco RI. As alternatively starting plasmid, there is chosen one which, after digestion with Bam HI and Eco RI, has a length of about 9.1 kb.

(1b) Preparation of the mutagenesis mix and mutagenesis procedure.

The starting plasmid prepared according to 1a or 1a' is treated with the enzymes Bcl I and Sac I and the larger fragment obtained preparatively by gel electrophoresis. In a further batch, the starting plasmid is linearized by cleavage with Hind III. Both plasmid fragments are mixed (each 0.15 pmole) and denatured by heating for 2 minutes to 95° C. 75 pmole of a kinased oligonucleotide were previously added. The sequence of the oligonucleotide determines the mutein species to be obtained and is explained in more detail hereinafter (cf. formulae I to III). By treating this mixture at 60° C. for 30 minutes, the formation of heteroduplex molecules occurs. This mutagenesis procedure is subsequently carried out at 12° C. with the addition of the following reagents to the given end concentration: desoxynucleotide triphosphates 0.25 mM, ATP 1 mM, sodium chloride 0.1M, tris-HCl (pH 7.5) 6.5 mM, magnesium chloride 8 mM, β-mercaptoethanol 1 mM, Klenow fragment 0.125 U/ul and T4 ligase 0.0625 U/ul.

The incubation period is 4 hours. Subsequently, an aliquot of the batch, containing 0.0075 pmole of vector, is used for the transformation into Escherichia coli cells BMTU 2489 (DSM 4178). The transformed colonies are selected on nutrient medium with 25 μg/ml of kanamycin and 40 μg/ml X-Gal. The desired mutants are β-Gal negative (white) and are found at a rate of 8%. The purified colonies are used for the plasmid preparation and the so obtained plasmids are retransformed as described above. The so obtained white second transformant cells are used for plasmid preparation and the plasmid DNA is hybridized with the radioactively labelled oligonucleotide employed. Plasmids which, by washing of the hybridization filter at 50° C., still show positive radioactive results, are plasmids which contain the desired mutation. Crude extracts are prepared from cells which contain these plasmids. These contain small values of β-Gal activity (<0.5% of the cells with starting plasmid). These crude extracts are separated on SDS gels by electrophoresis and the protein bands are colored with Coomassie coloring material. The crude extracts from such plasmid-carrying cells, which contain the desired β-Gal mutant gene, display a prominent β-Gal band which migrates in the gel identically with the starting plasmid from the crude extract and has the same size.

(1c) Preparation of the mutein β-Gal Tyr$_{503}$→Glu

There is used an oligonucleotide with the sequence

5' TGC CCG ATG GAA GGG CGC GTG 3'     (I)

which, at the amino acid codon position 503, contains GAA instead of TAC in the wild type lacZ gene. A Glu residue is coded at this position instead of Tyr. Plasmids which carry this desired mutation possess one Rsa I cleavage site less than the starting plasmid.

(1d) Preparation of the mutein β-Gal Glu$_{461}$→Ala and Tyr$_{503}$→Phe

There are used the two oligonucleotides of the sequence

5' TG GGG AAT GCA TCA CGC CA 3'     (II)

which, at the amino acid codon position 461, contains GCA instead of GAA in the wild type lacZ gene and

5' TGC CCG ATG TTT GCG CGC GTG 3'     (III)

which, at the amino acid codon position 503, contains TTT instead of TAC in the wild type lacZ gene. Plasmids which carry this desired mutation possess one Hind I and one Rsa I cleavage site less than the starting plasmid.

EXAMPLE 2

Comparison of native β-galactosidase and Gal muteins 2.1. Purification from Escherichia Coli biomass Cells from Escherichia coli with genetic information for native β-Gal and cells of the transformed Escherichia coli containing a plasmid which was obtained according to (1c) or (1d) is produced in an appropriate nutrient medium in 10 liter fermenters. The isolation of the β-Gal is carried out according to the process of G. R. Craven, E. Steers Jr. and C. B. Anfinsen (J. Biol. Chem., 240, 2468–2477/1965). It includes the steps of ammonium sulphate precipitation, gel filtration and anion exchange chromatography. In the case of purification according to the same process, in all purification steps the Gal muteins do not behave differently from native β-Gal. Because of the missing enzyme activity, the enrichment of the muteins is controlled by high resolution gel filtration on a TSK G4000 column (see 2.3.1).

The high molecular weight of Gal proteins brings about, on the background of the other Escherichia coli proteins, a very characteristic protein peak which can be quantitatively evaluated over all purification steps.

2.2 Enzymatic activity 2.2.1. Test procedure for the determination of the enzyme activity of β-galactosidase

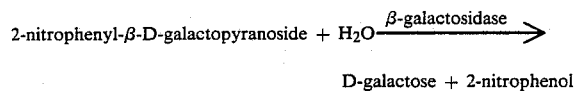

2-nitrophenyl-β-D-galactopyranoside + H$_2$O $\xrightarrow{\beta\text{-galactosidase}}$ D-galactose + 2-nitrophenol The 2-nitrophenol formed is measured at Hg 405 nm.

Solutions

1. Potassium phosphate buffer (0.05 mole/liter; pH 7.8):

(a) dissolve 0.68 g. monopotassium dihydrogen phosphate in double distilled water and make up to 100 ml;
(b) dissolve 1.14 g. dipotassium monohydrogen phosphate trihydrate in double distilled water and make up to 100 ml. Solution (b) is adjusted to pH 7.8 with Solution (a).
2. Magnesium chloride solution (10 mMole/liter):
dissolve 203.3 mg magnesium chloride hexahydrate (M 5833) in 100 ml double distilled water.
3. Nitrophenyl-β-D-galactopyranoside solution:
dissolve 5.9 mg 2-nitrophenyl-β-D-galactoside in 1 ml of buffer (1) (the solution should only be pale yellow colored).
4. Mercaptoethanol solution:
make up 69.8 ml 2-mercaptoethanol with double distilled water to 100 ml.
Sample solution:
Parent solutions of native β-galactosidase and of β-Gal mutein are diluted in buffer 1.
Carrying out:
Wavelength: Hg 405 nm; light path: 1 cm
Test volume: 2.98 ml., temperature: 37° C.

| into plastic cuvettes pipette: | | blank | sample |
|---|---|---|---|
| buffer | (1) | 2.20 ml. | 2.20 ml. |
| magnesium chloride | (2) | 0.300 ml. | 0.300 ml. |
| 2-nitrophenyl-β-D-galactosidase | (3) | 0.400 ml. | 0.400 ml. |
| mercaptoethanol | (4) | 0.030 ml. | 0.030 ml. |
| mix, temper and check predetermined temperature in the cuvette. Start reaction with | | | |
| buffer | (1) | 0.050 ml. | — |
| sample | | — | 0.050 ml. |
| mix, monitor change of absorbance and calculate ΔE/min. from the linear region. | | | |

Calculation:

$$\text{activity} = \frac{2.98}{0.05} \times \Delta E/\text{min} \ [U/\text{ml of sample solution}]$$

$$\epsilon_{405} = 3.5 [\text{mMole}^{-1} \times 1 \times \text{cm}^{-1}]$$

Figure 2:
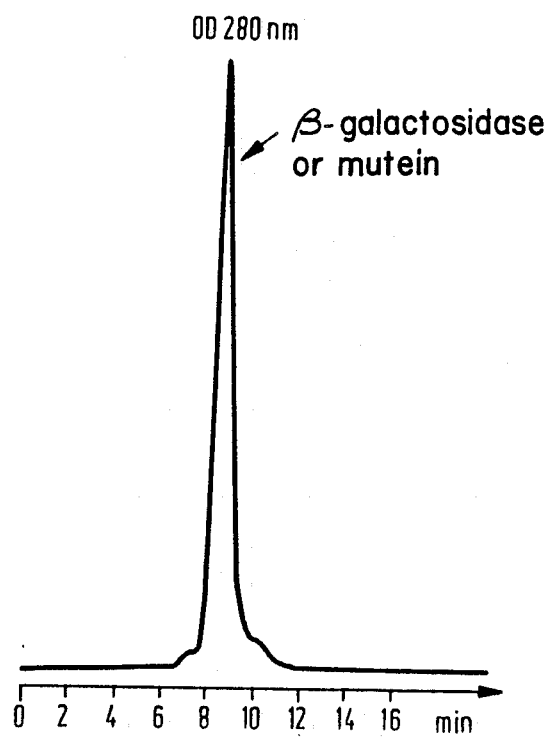
FIG. 2 is a gel filtration chromatogram according to Example 2.3.2.
Figure 3:
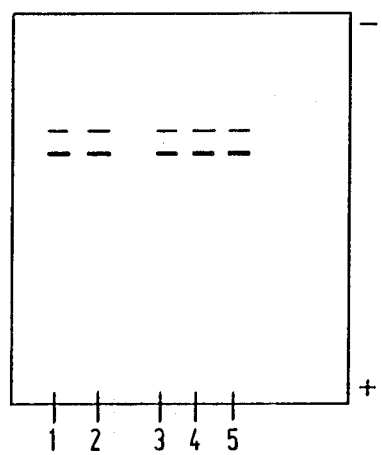
FIG. 3 is a polyacrylamide gel electropherogram according to Example 2.3.3.
Figure 4A:
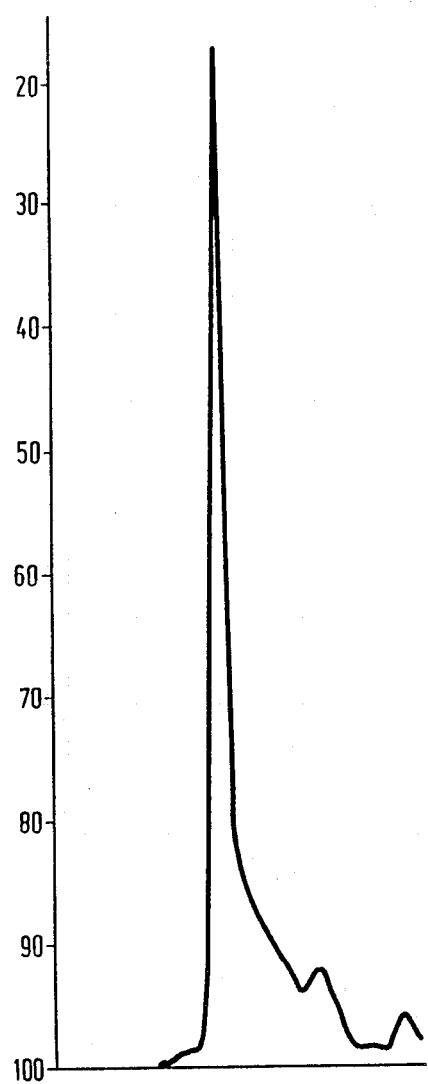
FIGS. 4(a) and (b) are each cross-linking profiles of (a) Gal mutein Phe 503 and (b) native β-galactosidase with mouse Fab.
Figure 4B:
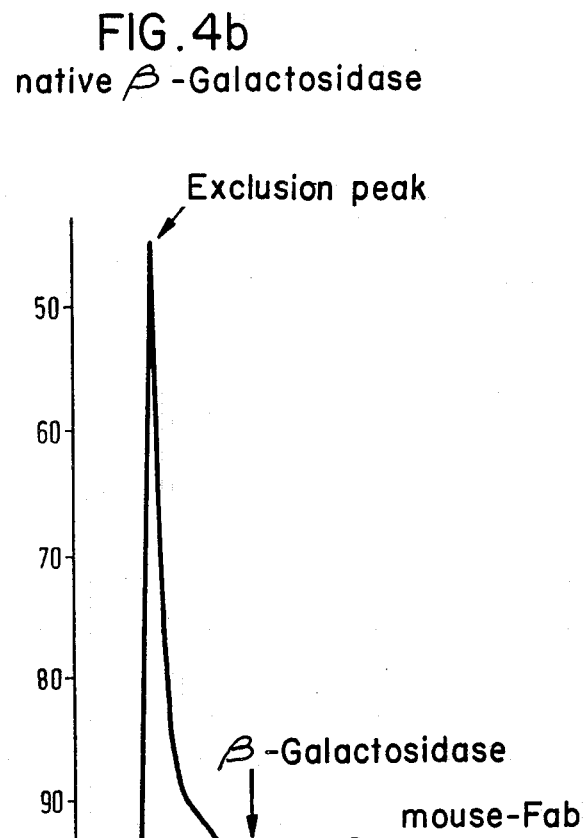

2.2.2 Results of the activity determinations.
Native β-Gal 600-650 U/mg protein
Gal mutein (Glu 503) <0.2 U/mg protein
Gal mutein (Ala 461/Phe 503) <0.2 U/mg protein
2.3. Analysis by high resolution analytical methods.
2.3.1. Anion exchange chromatography
Separation column MonoQ HR5/5 (Pharmacia)
Buffer A 20 mM Tris/HCl, pH 7.6
Flow rate 1 ml/min.
Paper advance 0.5 cm/min
Gradient form see FIG. 1
UV monitor 280 nm
Ambient temperature
Result: Native β-Gal and typical Gal muteins, such as Gal mutein (Glu 503) or Gal mutein (Ala 461/Phe 503), give, without differentiation, the chromatogram of FIG. 1.
2.3.2. Gel filtration
Separation column TSK G4000 SW, 7.5×300 mm (LKB)
Buffer 0.1M potassium phosphate/0.1% sodium azide, pH 6.8
Flow rate 1 ml/min.
Paper advance 0.5 cm/min.
UV monitor 280 nm
Ambient temperature
Results: Native β-Gal and typical Gal muteins, such as Gal mutein (Glu 503) or Gal mutein (Ala 461/Phe 503), give, without differentiation, the chromatograph of FIG. 2. By calibration of the separation column with calibration proteins of known molecular weight, a molecular weight of about 520,000 can be ascribed to the native β-Gal and to the Gal muteins.
2.3.3. Polyacrylamide gel electrophoresis
Electrophoresis apparatus: Phast system (Pharmacia)
Gradient gel 8-25% (Pharmacia)
Buffer conditions for native electrophoresis
Carrying out according to the Phast system handbook
of Pharmacia
Coloration with Coomassie dyestuff.
Result: The preparation of native β-Gal and of Gal muteins purified according to 2.1 do not give different band patterns, as can be seen from FIG. 3.
2.4. Characterization of Gal muteins by behavior in the case of coupling with mouse Fab
Purified preparation of Gal mutein was coupled with mouse Fab as described in Example 3. Before gel chromatography on SEPHAROSE 6B, a sample (50 μl) of the coupling batch was analyzed by high resolution gel chromatography on TSK G4000. The cross-linking profile (see FIG. 4a) obtained characterized the molecular weight distribution of the conjugate mouse Fab-Gal mutein. FIG. 4b shows a corresponding profile for a conjugate batch of mouse Fab coupled with native β-Gal. Result: In the case of coupling with mouse Fab, Gal mutein (Glu 503) behaves in the same way as native β-Gal, i.e., the SH groups of the Gel mutein are just as accessible for the bridging with the maleinimide coupling reagent as those of native β-Gal. Analogous findings were obtained for the Gal mutein (Phe 503).
The difference of the profiles of 4a and 4b is not significant since, for different native β-Gal batches and different coupling batches, similar small differences are unavoidable.
2.5 Testing of the immune reactivity towards sheep anti-β-Gal antibody
2.5.1 Test procedure
Test principle: To the plastic wells of a microtitre plate a polyclonal sheep anti-β-Gal-IgG antibody is adsorbed. Samples of a dilution series of β-Gal and of Gal mutein are placed into such coated wells. Immune-reactive protein binds to the well proportionally to the concentration of the dilution. After washing the wells, the particular bound immune-reactive protein is mixed with a solution of peroxidase-labelled sheep anti-β-Gal-Fab. Peroxidase conjugate now binds to the solid phase proportionally to the already well-bound amount of immune-reactive Gal protein. After renewed washing, the particular well-bound POD activity is developed by the addition of substrate such as ABTS ® and measured quantitatively with a photometer for microtiter plates.
Carrying out of the test:
1st step: Into each well of a microtiter plate is pipetted 0.2 ml of a solution of 10 μg sheep anti-β-Gal IgG per 1 ml of 40 mM potassium phosphate buffer (pH 7.4) and incubated for 50 minutes at ambient temperature.
2nd step: Each well is sucked out with a cannula and filled with 0.3 ml of a solution of 10 mg bovine serum albumin in buffer A (50 mM potassium phosphate buffer/100 mM sodium chloride (pH 7.5))

and incubated for 60 minutes at ambient temperature.

3rd step: The wells are sucked empty and every 2 wells filled with 0.2 ml of dilutions containing 0, 5, 10, 20, 30 and 40 ng β-Gal or Gal mutein/1 ml of buffer A containing 0.1% of bovine serum albumin and incubated for 60 minutes at ambient temperature.

4th step: All wells are sucked out, each filled with 0.3 ml of buffer A and again sucked out. 0.2 ml of a solution of peroxidase-sheep anti-β-Gal-Fab in buffer A/0.1% bovine serum albumin are then pipetted into each well (peroxidase content 100 mU/ml) and incubated for 60 minutes at ambient temperature.

5th step: All wells are sucked out, washed twice with buffer A and then each one filled with 0.2 ml substrate solution with 100 mg ABTS ® (Boehringer Mannheim GmbH) in 0.1M potassium phosphate-/citrate buffer (pH 4.4) and incubated for 60 minutes at ambient temperature.

6th step: The absorbance of the colored solution in the wells measured with a photometer for microtiter plates at 405 nm.

Figure 5:
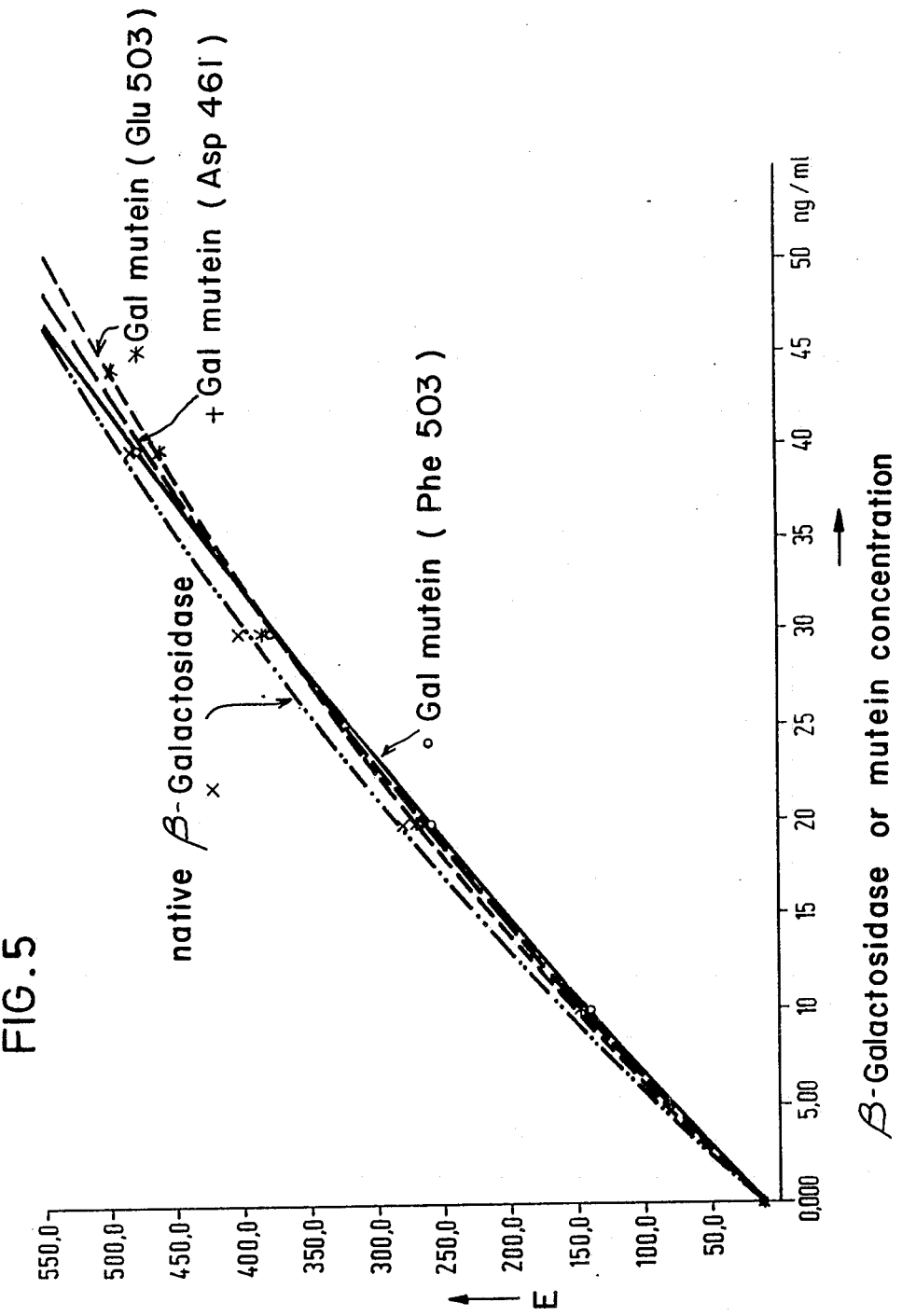
FIG. 5 is a graphic illustration of the immune reactivity of Gal muteins and native β-Gal.

Evaluation:

The mean value of the double determination of each protein dilution is plotted on the ordinates of a diagram against the respective protein concentration plotted on the abscissa. The points are joined by a fitting curve. FIG. 5 shows typical graphs which are obtained for β-Gal and Gal muteins with (this carrying out of) the test.

2.5.2 Result:

FIG. 5 shows graphically the dependency of the absorbance in the enzyme immune test of the amount of protein on β-Gal and Gal mutein. Within limits of error the curves for the investigated Gal muteins are identical with those of native β-Gal generated with an antibody which is obtained by immunization of sheep with native β-Gal. In other words, the immune determinants on the surface of the muteins cannot be diferentiated from those of native β-Gal.

EXAMPLE 3

Preparation of mouse Fab-β-galactosidase conjugate

The covalent coupling of β-galactosidase to Fab fragments takes place according to the instructions of T. Kitagawa in "Enzyme Immunoassay", E. Ishikawa, T. Kawai and M. Miyai eds., Igaku-Shoin, Tokyo/New York, 1981, pages 81-89: 10 mg Fab protein are dissolved in 2 ml. 0.05M phosphate buffer (pH 7.0) and mixed with 75 ul of a solution of N-(m-maleinimidobenzoyloxy)-succinimide (5 mg/ml) in tetrahydrofuran. The mixture is incubated for 30 minutes at ambient temperature and occasionally shaken. By passing the reaction batch over a gel chromatography column filled with 15 ml SEPHADEX G25 (Pharmacia), the reacted Fab is separated from the excess of reagent. The working buffer is 10 mM phosphate buffer (pH 6.2).

To the maleinimidohexanoylated Fab (8 mg Fab protein) are added 20 mg β-galactosidase (*Escherichia coli*) in 2 ml of 0.075M phosphate buffer (pH 7.0) and incubated for 2 hours at ambient temperature. The reaction product is purified by gel chromatography on SEPHAROSE 6B (Pharmacia). Column dimensions: 2×50 cm; chromatography buffer 0.02M phosphate/1 mM magnesium chloride/0.1% sodium azide/0.1% sodium chloride). The active conjugate fractions elute from the column at molecular weights of 590,000 to about 2,500,000. The fractions most appropriate for the test are determined therefrom by trial in immuno-assays as in example 4. The most favorable fractions are combined to give a pool.

EXAMPLE 4

Determination of thyreotropin (TSH) in human sera in the presence of disturbance factors against the labelling enzyme β-galactosidase The determination is carried out with a dry chemical reagent carrier in a one-step test according to the double antibody solid phase sandwich test principle (DASP) in rotor insert elements with a centrifugal analyzer with the analysis apparatus described in published Federal Republic of Germany Patent Specification No. 34 25 008.

1.1. Preparation of the reagent solutions 1.1. Buffer I 50 mMole/liter potassium phosphate buffer (pH 6.0), prepared by mixing 50 mMole/liter dipotassium monohydrogen phosphate solution and 50 mMole/liter monopotassium dihydrogen phosphate solution until a pH value of 6.0 is achieved.

1.2. Buffer II

Buffer II is prepared like buffer I but with the difference that the pH value is adjusted to 7.5 and that the buffer additionally contains 10 g/liter of bovine serum albumin and 150 mMole/liter of sodium chloride.

1.3. Receptor $R_1$ solution, bindable with TSH

As receptor $R_1$, there is used a monoclonal mouse anti-TSH antibody. The ascites fluid containing this antibody is mixed with ammonium sulphate to a concentration of 1.8 mole/liter. The precipitate is taken up in a buffer of 15 mmole/liter sodium phosphate (pH 7.0) and 50 mMole/liter sodium chloride. The TSH-bindable solution thus obtained is subjected to a passage over DEAE-cellulose. The eluate so obtained, containing TSH-bindable antibody, is diluted with buffer II to a protein concentration of 1 μg/ml.

1.4. Enzyme-labelled repceptor $R_3$ solution

As receptor $R_3$, there is also used a monoclonal mouse anti-TSH antibody which, however, recognizes a different determinant than receptor $R_1$. The ascites fluid containing this antibody is purified as described in 1.3. The complete antibody is cleaved, forming, inter alia Fab fragments in known manner according to the method of R. R. Porter, Biochem. J. 73, 119/1979. The Fab fragments so obtained are coupled with β-galactosidase according to Example 3. The receptor $R_3$ β-Gal conjugate solution is diluted in buffer II to a concentration of 500 mU/ml (measured with 0-nitrophenyl-β-galactoside at 37° C.).

1.5. Inactive enzyme solution; β-Gal mutein (Glu 503)

The β-Gal mutein produced by precise alteration of the native labelling enzyme β-galactosidase (in receptor $R_3$) by point mutation in codon 503, which is enzymatically inactive but is unchanged in its surface structure and thus possesses the antigenic determinants like the native enzyme, is diluted in buffer II to a concentration of 1 mg/ml.

1.6. Receptor $R_2$ solution

Sheep anti-mouse-Fcγ antiserum is mixed with ammonium sulphate ad 1.8 mole/liter. The precipitate is taken up in a buffer of 15 mMole/liter sodium phosphate (pH 7.0) and 50 mMole/liter sodium chloride. The solution thus obtained is subjected to a passage over DEAE-cellulose. The eluant containing the specific antibody is diluted in buffer I to a protein concentration of 50 μg/ml.

1.7. Substrate solution

| | |
|---|---|
| chlorophenol red-β-galactoside (prepared according to Federal Republic of Germany Patent Specification No. 33 45 748) | 5 mMole/liter (3.06 g/1.) |
| HEPES | 70 mMole/liter (16.7 g/1) |
| sodium chloride | 154 mMole/liter (9 g/1) |
| bovine serum albumin | 0.3% (3 g/1) |
| TWEEN 20 | 0.2% (2 g/1) |
| pH (with sodium hydroxide) | 7.25 |

2. Preparation of reagent carriers 2.1. Reagent carrier 1 (without mutein)

40 μl of a solution which, per liter, contains 10 mMole sodium phosphate (pH 7.3; 37° C.), 2 mMole magnesium chloride, 9 g sodium chloride, 5 g bovine serum albumin, 5 mg anti-TSH monoclonal antibody from the mouse (receptor $R_1$), 1000 U anti-TSH antibody (mouse) Fab fragment-β-galactosidase conjugate (receptor $R_3$ conjugate solution; activity determined with o-nitrophenyl-β-D-galactoside at 37° C.), is applied dropwise to a fleece which consists of commercially available polyester paper. Subsequently, it is dried at ambient temperature. Until used, the fleeces are kept at 4° C. and at a relative atmospheric humidity of 20%.

2.2. Reagent carrier 1' (addition of mutein)

The production takes place as for reagent carrier 1 except for the difference that, per liter of impregnation solution, there is present 25 mg β-Gal mutein (Glu 503).

2.3. Reagent carrier 2

Sheep antibodies against the Fc part of mouse antibodies (receptor $R_2$ solution) are fixed on to cellulose fleece according to the cyanogen bromide activation process (see Federal Republic of Germany Patent Specification No. 17 68 512), 10 μg of antibody being provided for fixing per gram of fiber material. Non-coupled antibody is removed by washing and the fleece is gently dried at ambient temperature. Storage of the fleece thus obtained takes place analogously to reagent carrier 1.

3. Carrying out of the determination

The determination with the help of these two reagent carriers 1 and 2 or 1' and 2 takes place with the device for carrying out analytical determinations described in Federal Republic of Germany Patent Specification No. 34 25 008.

Figure 6:
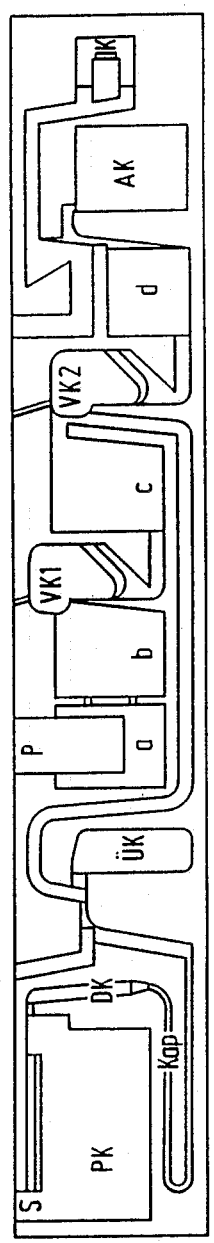
FIG. 6 is a schematic illustration of the centrifugal rotor insert used in Examples 4 and 5.

This describes a rotor insert element, as shown in FIG. 6, for centrifugal automatic analyzers, comprising a formed body which has a sample application chamber which is connected to a plurality of reagent fields, each of which contains an absorbent carrier material impregnated with a particular reagent, at lesat one mixing valve chamber and a measurement chamber, which together form a sample liquid transport path which runs radially from the inside towards the outside when the insert element is fixed on the rotor, and also has at least one further chamber for the reception of a liquid and a transport path which leads from this chamber to the measurement chamber and is at least partly identical with the sample liquid transport path.

The same liquid transport path thereby leads from a place where sample is added (S) in a sample application chamber (P) via a chamber (a), filled with an absorbent material containing a buffer, a chamber (c) and a first valve chamber (VK1) arranged between the chambers (a) and (c) to a second valve chamber (VK2) and from this, via chamber (d) and via a collection chamber (AK), to the measurement chamber (K). Reserve chamber (b) is present, but is not required in this embodiment. For the reception of a further liquid, there is provided a substrate chamber (PK), constructed as a pump chamber which is connected via a dosing device, comprising a dosing chamber (DK) and a capillary (Kap), and an overflow chamber (ÜK), with the second valve chamber (VK2).

For the determination of the absorbance aa (measurement signal including disturbing signal), there are used reagent carriers 1 and 2 and, for the determination of the absorbance bb (specific measurement signal without disturbing signal), there are used reagent carriers 1' and 2.

Reagent carrier 1 or 1' is placed on field c of the rotor insert element and reagent carrier 2 on field d. 40 ul of concentrated sample are thereby pipetted through an opening on the upper edge directly on to the field a. 270 ul of substrate solution are pipetted into chamber PK. By means of an appropriate centrifuging program, in which high speeds of rotation alternate with stopping, sample and substrate solution are then conveyed in the direction of the separating matrix and cuvette.

In the course of the program, the receptors $R_1$ and $R_3$ without or with mutein are thereby eluted by the sample liquid from field c and the homogeneous mixture subsequently brought to reaction. On field d, the complexes formed are bound via $R_1$ to the receptor $R_2$. The transfer of the sample from field c to d takes place within a very short period of time.

The substrate solution is divided into portions by the dosing chamber DK, the first of which serves for washing out excess, non-complexed conjugate.

Disturbing factors, which could cross-link $R_3$, are, in the case of the use of a 20 fold excess of β-Gal mutein, neutralized with regard to the native labelling enzyme and also washed out (use of reagent carrier R1').

The β-galactosidase activity bound to d via complex formation is proportional to the amount of TSH contained in the same or to the sample blank. This activity is determined with a further portion of substrate, the substrate thereby being in a 5 minute reaction to give colored products. The color formed and the further color development/minute in the liquid phase are measured in the cuvette at 576 nm.

Unter these conditions, the following results are obtained:

| | a | | b | |
|---|---|---|---|---|
| sample | OD [mE] | conc. [μU/ml.] | OD [mE] | conc. [μU/ml.] |
| TSH calibrator 0 μU/ml.[c] | 451 | 0 | 457 | 0 |
| TSH calibrator 9.6 μU/ml.[c] | 3331 | 19.6 | 3311 | 19.5 |
| human serum 1 | 669 | 1.5 | 725 | 1.8 |
| human serum 2 with anti-Gal disturbance factors | 2573 | 14.4 | 649 | 1.3 |

All measurements were carried out at λ=576 nm at a light path of 0.3 cm and recalculated to a layer thickness d=1 cm.

(a) TSH determination in the case of using reagent carrier 1

(b) TSH determination in the case of using reagent carrier 1' with β-Gal mutein for the neutralization of galactosidase-specific disturbance factors (c) TSH standard.

EXAMPLE 5

Determination of thyrotropin (TSH) in human sera

Lowering of non-specific blank values

The determination is carried out analogously to Example 4. All reagent solutions are identical except the solution described in Example 4 under 1.5. In this case, there is used an analyte-non-specific Fab conjugate solution labelled with inactive β-galactosidase mutein.

Preparation

The β-Gal mutein (Glu 503), produced by precision change of the native labelling enzyme β-galactosidase (in receptor $R_3$) by point mutation in codon 503, which is enzymatically inactive but is unchanged in its surface structure and thus possesses the same antigenic determinants as the native enzyme, is coupled, as described in Example 4 under 1.4, with the Fab part of an immunoglobulin which, however, is not binding-active for the analyte. The mutein-Fab conjugates thus obtained is diluted in buffer II to a concentration of 1 mg/ml.

The production of the reagent carriers and the carrying out of the determination also takes place analogously to Example 4. Serum factors which cause non-specific blank values are neutralized in the case of the use of excess immunological as well as enzymatically inactive mutein-Fab conjugate and also washed out (use of reagent carrier R1').

The β-galactosidase activity bound via complex formation to d is proportional to the amount of TSH contained in the sample or to the sample blank value. This activity is determined with a further portion of substrate, the substrate thereby being reacted in a 5 minute reaction to give colored products. The color formed and the further color development/minute in the liquid phase are measured in the cuvette at 576 nm.

Under these conditions, the following results are obtained:

| sample | a | b | Δ% |
| --- | --- | --- | --- |
| TSH-free[c] human serum | 485 ± 32 [mE] | 339 ± 11 [mE] | −30% |
| human serum[c] 19.6 μU/ml. | 3983 ± 166 [mE] | 3733 ± 1072 [mE] | — |
| TSH content calibration curve | 178 [mE/μU] | 173 [mE/μU] | −3% |

All measurements were carried out at λ=576 nm at a light path of 0.3 cm and recalculated to a layer thickness of d=1 cm.

(a) TSH determination in the case of the use of reagent carrier 1.

(b) TSH determination in the case of the use of reagent carrier 1' with mutein-Fab conjugate for the reduction of non-specific blank values.

(c) TSH standard.

It will be understood that the specification and examples are illustrative but not limitative of the present invention and that other embodiments within the spirit and scope of the invention will suggest themselves to those skilled in the art.

We claim:

1. A mutein of β-galactosidase which is enzymatically inactive and immunologically active, characterized by an amino acid mutation at amino acid 503 which is normally Tyr of said β-galactosidase, said mutein having no more than 1% of the enzymatic activity of native β-galactosidase.

2. The mutein of claim 1, further comprising an additional mutation at amino acid 461 which is normally Glu.

3. The mutein of claim 1, wherein said mutation is a change of Tyr at amino acid 503 by one of Phe, Glu or Ser.

4. The mutein of claim 2, wherein said mutein has a mutation at amino acid 461 in which Glu is changed to one of Ser, Ala, Asp or Tyr, and a mutation at amino acid 503 in which Tyr is changed to one of Phe, Glu, or Ser.

5. Process for producing an enzymatically inactive, immunologically active β-galactosidase mutein which contains a mutation at amino acid 503 which is normally Tyr, comprising treating a plasmid coding for native β-galactosidase causing site directed mutagenesis in said plasmid resulting in a mutation in the portion of said plasmid coding for β-galactosidase amino acid 503, and expressing said plasmid to produce said mutein.

6. Process of claim 5, further comprising causing site directed mutagenesis of said plasmid at the portion thereof coding for β-galactosidase amino acid 461, which is normally Glu.

7. Process of claim 6, wherein said site directed mutagenesis comprises mutagenesis of the portion coding for Glu at amino acid 461 to code for one of Ser, Ala, Asp or Tyr.

8. Process of claim 5, wherein said site directed mutagenesis comprises mutagenesis of the portion coding for Tyr at amino acid 503 to code for one of Phe, Glu, or Ser.

9. Process of claim 5, wherein said site directed mutagenesis comprises mutagenesis of the portion coding for Glu at amino acid 461 to code for one of Ser, Ala, Asp or Tyr and the portion coding for Tyr at amino acid 503 to code for one of Phe, Glu, or Ser.

10. An immunoassay method for determining an analyte in a liquid sample suspected of containing a potentially interfering binding substance, comprising:

contacting said liquid sample with
 (i) a labeled conjugate of (a) enzymatically acitve B-galactosidase and (b) an antibody or bindable fragment thereof which specifically binds to the analyte to be determined, and
 (ii) an amount of enzymatically inactive, immunologically active B-galactosidase mutein characterized by an amino acid mutation at amino acid 503 which is normally Tyr, said mutein having no more than 1% of the enzymatic activity of native B-galactosidase and effective to specifically bind any said potentially interfering binding substance capable of binding immunologically active B-galactosidase; and measuring bound or free labeled conjugate in order to determine the amount of analyte in said sample.

11. Method of claim 10 wherein said contacting step further comprises adding a sufficient amount of a Fab fragment, which does not bind to said analyte, effective to specifically bind any said potentially interfering binding substance capable of binding said antibody or bindable fragment of said labeled conjugate.

12. Method of claim 10, wherein said mutein is added in the form of a chemically bound conjugate of said mutein and a Fab fragment of a non-analyte specific immunoglobulin.

13. Method of claim 10, wherein said mutation further comprises an additional mutation at amino acid 461 which is normally Glu.

14. Method of claim 10, wherein said mutation is a change of Tyr at amino acid 503 by one of Phe, Glu or Ser.

15. Method of claim 13, wherein said mutation is a change of Glu at amino acid 461 to one of Ser, Ala, Asp or Tyr.

16. Method of claim 10, wherein said mutein comprises a change of Tyr at amino acid 503 by one of Phe, Glu or Ser and a change of Glu at amino acid 461 to one of Ser, Ala, Asp or Tyr.

17. Reagent useful in eliminating a potentially interfering binding substance in a B-galactosidase labeled immunoassay for determining an analyte in a liquid sample, comprising:
   (i) an enzymatically inactive, immunologically active B-galactosidase mutein characterized by an amino acid mutation at amino acid 503 which is normally Tyr, said mutein having no more than 1% of the enzymatic activity of native B-galactosidase and wherein said mutein specifically binds to any said potentially interfering binding substance capable of binding to immunologically active B-galactosidase, and
   (ii) a Fab fragment which does not bind to said analyte but which specifically binds to any said potentially interfering binding substance capable of binding to the antibody or bindable fragment thereof said labeled conjugate.

18. Reagent of claim 17, wherein said mutein and said Fab fragment are chemically bound together.

19. Reagent of claim 17, wherein said mutein further comprises an additional mutation at amino acid 461 which is normally Glu.

20. Reagent of claim 17, wherein said mutation is a change of Tyr at amino acid 503 by one of Phe, Glu or Ser.

21. Reagent of claim 19, wherein said mutation is a change of Glu at amino acid 461 to one of Ser, Ala, Asp, or Tyr.

22. Reagent of claim 19, wherein said mutein comprises a change of Tyr at amino acid 503 by one of Phe, Glu or Ser and a change of Glu at amino acid 461 to one of Ser, Ala, Asp, or Tyr.

* * * * *

UNITED STATES PATENT AND TRADEMARK OFFICE
CERTIFICATE OF CORRECTION

PATENT NO. : 4,963,469

DATED : October 16, 1990

INVENTOR(S) : Ralf Mattes et al.

It is certified that error appears in the above-identified patent and that said Letters Patent is hereby corrected as shown below:

On the title page, in the title:
    Change "Muetin" to -- Mutein --.

Column 1, line 3: change "Muetin" to -- Mutein --.

Column 8, line 34: change "Gel" to -- Gal --.

Column 11, line 54: change "lesat" to -- least --.

Column 12, line 58: change "9.6 uU/ml" to -- 19.6 uU/ml --.

Column 16, line 25 (claim 17), before "said" add -- of --.

Signed and Sealed this

Eleventh Day of August, 1992

*Attest:*

DOUGLAS B. COMER

*Attesting Officer*   *Acting Commissioner of Patents and Trademarks*